United States Patent [19]

Bargmann et al.

[11] Patent Number: 4,935,341
[45] Date of Patent: Jun. 19, 1990

[54] DETECTION OF POINT MUTATIONS IN NEU GENES

[75] Inventors: Cornelia I. Bargmann, Arlington; Robert A. Weinberg, Brookline, both of Mass.

[73] Assignee: Whitehead Institute for Biomedical Research, Cambridge, Mass.

[21] Appl. No.: 871,102

[22] Filed: Jun. 4, 1986

[51] Int. Cl.$^5$ .............................................. C12Q 1/68
[52] U.S. Cl. ..................................... 435/6; 435/803; 436/501; 536/27; 935/9; 935/78
[58] Field of Search .............. 536/27; 436/501; 435/6, 435/803; 935/78, 9

[56] References Cited

U.S. PATENT DOCUMENTS 4,172,124  10/1979  Koprowski et al.
4,535,058   8/1985  Weinberg et al. ................ 935/77 X

FOREIGN PATENT DOCUMENTS 0108564   5/1984  European Pat. Off.

OTHER PUBLICATIONS

Bargmann, C. I. et al. Cell, 45 Jun. 6, 1986 pp. 649–657.
Bargmann, C. I. et al Nature 319: 1986 pp. 226–230.
Studencki, A. B. et al, DNA 3: 1984, pp. 7–15.
Hung, M-C et al, Proc. Natl. Acad. Sci. U.S.A. 83 1986, pp. 261–264.
Yamamoto, T. et al, Nature 319: 1986, pp. 230–234.
Semba, K. et al, Proc. Natl. Acad. Sci. U.S.A. 82 1985, pp. 6497–6501.
Schechter, A. L. et al, Science 229 1985, pp. 976–978.
Shih et al., "Transforming genes of carcinomas and neuroblastoma introduced into mouse fibroblasts," *Nature*, 290: 261–264 (1981).
Seeger et al., "Association of Multiple Copies of the N-myc Oncogene with Rapid Progression of Neuroblastomas," *N. E. J. of Medicine*, 313(18): 1111–1116 (1985).
Coussens et al., "Tyrosine Kinase Receptor with Extensive Homology to EGF Receptor Shares Chromosomal Location with neu Oncogene," *Science*, 230: 1132–1139 (1985).
Drebin et al., *Nature*, 312:545–548 (1984).
King et al., *Science*, 229:974–976 (1985).
Fukushige et al., *Mol. Cell. Biol.* 6:955–958 (1986) Mar.
Yokota et al., *The Lancet*, 765–767 (1986) Apr. 5.
Drebin et al., *Cell*, 41:695–706 (1985).
Bargamann, C. I. et al., *Chemical Abstracts*, 105(7), Abstract 55561a 8/1886.
Schechter, A. L. et al., *Nature*, 312:513–516 (1984).
Guerrero, I. et al., *Science*, 225:1159–1162 (1984).

*Primary Examiner*—Amelia Burgess Yarbrough
*Attorney, Agent, or Firm*—Hamilton, Brook, Smith & Reynolds

[57] ABSTRACT

Oligonucleotide probes reactive with regions of neu oncogenes of mammalian origin in which the mutation causing activation of such oncogenes is contained are described, as are methods for their use in detecting the presence of neu oncogenes in tumor cells. Antibodies specific for gene products encoded by neu oncogenes are also described.

7 Claims, 6 Drawing Sheets p185—

FIG.3

```
normal                                                        val
                                                              GTG
glu gln arg ala ser pro val thr phe ile ile ala thr val  :    gly val    aa 666
GAG CAG AGA GCC AGC CCG GTG ACA TTC ATC ATT GCA ACT GTA  :    GGC GTC
                                                              GAG
transforming                                                  glu leu leu phe leu ile leu val val val val gly ile leu ile lys arg arg    aa 683
CTG CTG TTC CTG ATC TTA GTG GTG GTC GTT GGA ATC CTA ATC AAA CGA AGG
```

FIG. 4

A) ACGCCCACTACAGTTGCAAT     nucleotides 1999-2018, wild-type sequence

B) ACGCCC*TCTACAGTTGCAAT     nucleotides 1999-2018, $T_{2012}$ to A

C) CCGTCCTCAGCTGTGACC     nucleotides 996-1013, control probe

D) ACGCCC*CCTACAGTTGCAAT     nucleotides 1999-2018, $T_{2012}$ to G

DETECTION OF POINT MUTATIONS IN NEU GENES

SPONSORSHIP

The work described herein was supported by a grant from the National Cancer Institute and grants from the American Business Cancer Research Foundation.

BACKGROUND

An increasing body of evidence implicates somatic mutations as causally important in the induction of human cancers. These somatic mutations may accumulate in the genomes of previously normal cells, some of which may then demonstrate the phenotypes associated with malignant growth. Such oncogenic mutations may include a number of different types of alterations in DNA structure, including deletions, translocations and single nucleotide alterations. The latter, also known as point mutations, may frequently intervene in carcinogenesis, in that a variety of mutagenic chemicals induce such mutations. In addition, such mutations may occur spontaneously as a result of mistakes in DNA replication.

Point mutations have been directly implicated in the causation of 10–15% of human tumors. These tumors carry oncogenes of the ras gene family, which differ from their normal cellular counterpart protooncogenes by the presence of a point mutation at one of several sites in these genes. These mutations represent qualitative changes in the tumor cell genome which distinguish these cells from normal cells and provide a basis for diagnosis of the genetic origin of a tumor under study. Identification of the mutations that have created active oncogenes may provide important diagnostic and prognostic clues for tumor development. For example, a number of mutations have been found to alter the 12th codon of the ras oncogenes, causing replacement of a normally present glycine by any of a number of alternative amino acid residues. Such amino acid substitutions do not have equivalent effects; some substitutions (e.g., valine) create a potent transforming allele while others (e.g., proline) have only a limited effect on cellular phenotype. Thus, the identity of a particular nucleotide substitution may be a strong determinant of the behavior of the tumor cell (e.g., its rate of growth, invasiveness, etc.). As a result, DNA probes of oncogene mutations have promise as diagnostic reagents in clinical oncology.

Such probes are useful, however, only if a region of a gene of interest in which point mutations are likely to occur has been identified. Unless identification of such a region has been made, it is impractical to use oligonucleotide probes of limited size (e.g., 10–20 nucleotides long) to scan an entire gene, which might well be 30,000 or more base pairs long; for example, if a 15-nucleotide probe were used to scan the entire length of a gene 3,000–5,000 base pairs long, 3000–5000 separate probes would be required.

Thus, although DNA probes of oncogene mutations have potential as diagnostic tools, they cannot be used effectively unless a discrete region of mutation in the gene, which is causally related to activation of the gene's oncogenic function, has been identified. Without such localization of the region of mutational activation, use of DNA probes specific for point mutations is impractical.

SUMMARY OF THE INVENTION

This invention relates to assessment of cellular DNAs to determine whether they carry lesions or alterations in a neu gene which result in the activation of the protooncogene, and its conversion to an oncogene. Oligonucleotide probes specific for nucleotide sequences of the region in which the activation mutation(s) resides, which can be used to determine the presence of an oncogene of the neu family are described, as are methods for their use.

It has been determined that the rat neu protooncogene, which encodes a protein resembling a growth factor receptor, is converted into an oncogene by a single nucleotide alteration or point mutation. This point mutation was initially seen in a rat neuroblastoma induced by transplacental exposure to a carcinogen (e.g., ethylnitrosourea) and found to affect the amino acid sequence of the transmembrane region of the p185 encoded by the DNA. That is, a valine present in the normal protein is replaced by a glutamic acid residue.

Oligonucleotide probes used to assay for similar point mutations suspected to be present in seven additional neu oncogenes, each of which arose in a separate, independently induced tumor, demonstrated the presence of the same activating mutations in all seven neu oncogenes. The same amino acid substitution (glutamic acid replacing valine) resulted in these cells.

The human homolog of this gene (also known as c-erbB2 or HER2) is thought to achieve an oncogenic state through the action of a similar mechanism: alteration of a single nucleotide in the normal cellular DNA sequence (the protooncogene), resulting in activation of the oncogene. The activating lesion found can be identified in the DNA of a variety of spontaneously arising human tumors through the use of oligonucleotide probes constructed to be specifically reactive with the region of the human neu gene corresponding to the region in the rat neu oncogene known to contain the activating mutations. Identification in human tumor cells of the activating point mutation responsible for conversion of the protooncogene into the neu oncogene can serve as the basis for construction of oligonucleotide hybridization probes useful in testing human tumor DNAs for the presence or absence of point mutations responsible for activation of neu oncogenes. These hybridization probes can be used in detecting the occurrence of the neu protooncogene and of the neu oncogene in cells and in determining the profile of oncogene activations in human tumor specimens. Such oligonucleotide probes are described, as are methods for their use in detecting the presence or absence of neu oncogenes in tumor cells. Antibodies specific for the p185 protein encoded by the neu oncogene, which can be used to detect the occurrence of the neu oncogene, are also described.

BRIEF DESCRIPTION OF THE DRAWINGS

FIG. 3 shows nucleotides 1968 to 2073 and the predicted amino acid sequence for the normal rat neu gene and the transforming rat neu gene.

FIG. 4 shows the nucleotide sequence of oligonucleotide probes corresponding in sequence to (a) the wild type (normal), (b) the mutant neu version of the neu gene, (c) DNA from DHFR G8, and (d) a modified version of the mutant neu gene in which there is a T to G transversion.

DETAILED DESCRIPTION OF THE INVENTION

Figure 1:
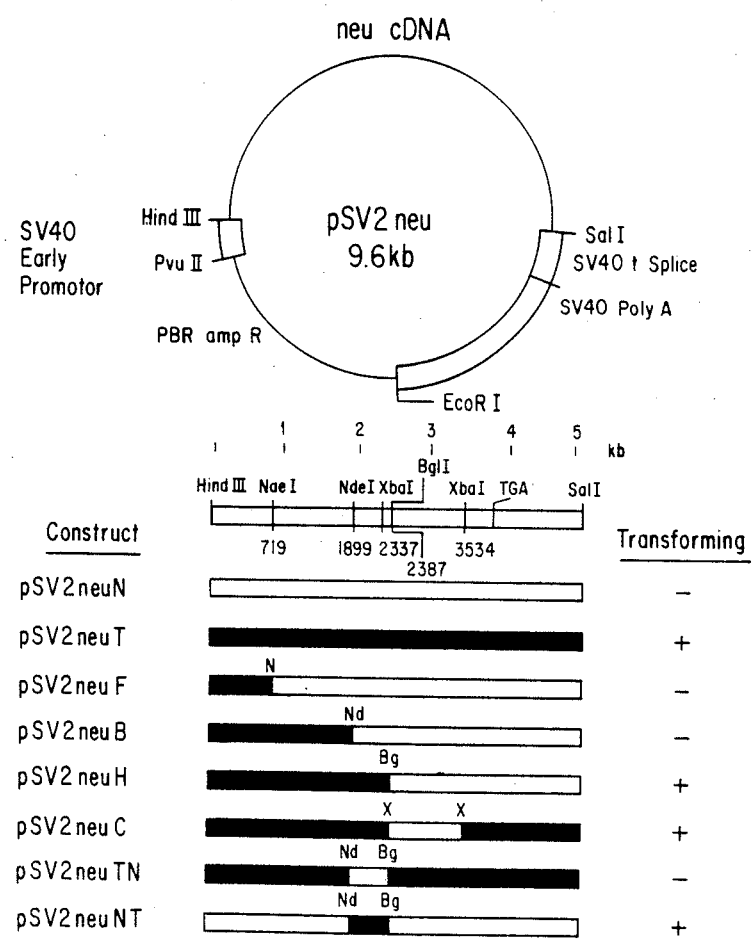
FIG. 1 is a schematic representation of pSV2neu, created by inserting the neu gene cDNA indicated into the pSV2 expression vector.

It is now known that cellular genes other than the ras genes can be converted into oncogenes by point mutations. It has recently been shown that the rat neu protooncogene, which encodes a protein resembling a growth factor receptor, can also be converted into an oncogene by a single nucleotide alteration. Thus, it has been shown that the neu protooncogene (i.e., the nucleotide sequence present in the normal genome of normal non-tumor cells) can undergo mutational activation into its corresponding oncogene (i.e., the nucleotide sequence whose expression within a cell causes its conversion from a normal cell into a tumor cell) by a single nucleotide substitution. This point mutation, initially demonstrated in a rat neuroblastoma induced by transplacental exposure to ethylnitrosourea, has also been shown to occur in seven other neu oncogenes, each of which arose in a separate, independently induced tumor. Detection of the point mutations relied on the use of oligonucleotide probes specific for the region initially shown to contain the activating mutation. In all cases, the same amino acid substitution resulted: a valine normally present in the transmembrane region of the encoded p185 protein was replaced by a glutamic acid residue. This finding suggests that nucleotide substitution at only a limited number of sites in the neu protooncogene will result in its becoming an active oncogene.

Human versions of the rat neu genes have been isolated and are also referred to as c-erbB2 or HER2. Yamamoto, T. et al., Nature, 319:230–234 (1986); Coussens, L. et al., Science, 230:1132–1139 (1985). The DNA sequences of both the rat and the human clones predict a 1260 amino acid protein product of the neu gene.

Mutational activation of the human homologs of the rat neu genes, referred to here as the human neu oncogenes, is thought to occur through a similar mechanism: single nucleotide substitution or point mutation in the human neu gene. It is highly likely that the single nucleotide substitution occurs in the region of the human neu protooncogene that corresponds with the region in the rat neu oncogene shown to contain the activating mutations. It is possible to determine the presence or absence of the activating lesion in the DNA of a variety of spontaneously arising human tumors through the use of oligonucleotide probes specifically reactive either with regions unique to the neu oncogene or with regions unique to the corresponding neu protooncogene. That is, hybridization probes can be constructed which will react (hybridize) with a nucleotide sequence occurring in either a neu oncogene or its corresponding protooncogene (but not in both). Such probes can be used to test human tumor DNAs for the occurrence of a point mutation responsible for activation of the neu oncogene. For example, radiolabelled oligonucleotide probes can be used in the Southern blot hybridization procedure to detect activation of the neu oncogene in human tumors of clinical interest.

Because the p185 proteins encoded by neu oncogenes are different from those encoded by their corresponding protooncogenes, it is also possible to develop serological reagents, such as polyclonal antibodies or monoclonal antibodies, which are specific for the altered or the normal amino acid sequences in such proteins. These reagents can be used to provide highly sensitive test cells for the presence or absence of neu oncogenes by detecting the occurence of the mutated or altered gene products they encode.

As described below, the approach described above has been used successfully in identifying the point mutation which causes activation of the neu protooncogene in DNA from a chemically induced rat neuroblastoma. It has also been used to verify the occurrence of the same activating point mutations, suspected to be present, in seven other neu oncogenes (each having arisen in a separate, independently (chemically) induced tumor). The approach described can be used, with modification, in identifying point mutations which cause activation of human neu oncogenes. In addition, it is possible to develop serological reagents, such as polyclonal antibodies or monoclonal antibodies specific for the altered or the normal amino acid sequences of the proteins encoded, respectively, by a neu oncogene or its corresponding protooncogene. These reagents can be used to test cells for the occurrence of the encoded protein and thus for the presence or absence of the neu oncogene.

The neu gene family

Exposure of perinatal BDIX rats to a single dose of the alkylating agent ethylnitrosourea leads to a high incidence of neuroectodermal tumors. Rajewsky, M. F. et al., In:*Origins of Human Cancer*, Cold Spring Harbor Laboratory, 709–726 (1977); Rajewsky, M. F., In:*Recent Results in Cancer Research* 84:63–76 (1983). Up to 95% of animals mutagenized transplacentally after the fifteenth day of gestation or injected directly with ethylnitrosourea up to ten days after birth will develop central and peripheral nervous system tumors after a dose- and strain-dependent latency time. These tumors and the cell lines derived from these tumors display the characteristics of a wide variety of neural and glial cell types. Schubert, D., *Nature*, 249:224–227 (1974).

DNA isolated from four independently derived tumor cell lines of this type contains activated oncogenes which can be detected in an NIH 3T3 focus forming assay. The majority of oncogenes detected in this assay have been shown to be genetically altered versions of one of the three closely related ras genes (Varmus, 1984). However, the gene transferred from these neuro/gliobastomas is unrelated to the ras genes and has been designated neu.

Neu was first recognized to be a distinct gene by its association with the 185,000 dalton tumor antigen, p185, which is displayed on the surface of transfected cells. Neu is related in DNA sequence to the erbB gene, which encodes the epidermal growth factor (EGF) receptor, and antisera raised against the EGF receptor show some cross-reactivity with p185. However, detailed analysis has shown that neu bears only limited homology to erbB and that the two genes reside on different chromosomes. Schechter, A. L. et al., *Science*, 229:976–978 (1985). Thus, the neu gene is related to, but distinct from, the gene which encodes the EGF receptor.

cDNA clones of the neu oncogene have been isolated from cell lines transformed by this gene. Bargmann, C. I. et al., *Nature,* 319:226-230 (1986). Human versions of the same gene have also been isolated and termed variously c-erbB2 or HER2. The DNA sequences of these rat and human clones predict a 1260 amino acid protein product of the neu gene which is colinear with and 50% identical to the predicted amino acid sequence of the EGF receptor. By analogy to the EGF receptor, the neu product appears to be a transmembrane protein consisting of a cysteine-rich extracellular region of 650 amino acids, a transmembrane domain, and an intracellular portion of 580 amino acids consisting in part of a tyrosine kinase domain.

Biochemical studies of the p185 protein support these conclusions. p185 is glycosylated and accessible to antisera in intact cells, which is consistent with its being localized at the cell surface. It also has an associated tyrosine specific protein kinase activity. p185 does not, however, bind EGF and thus appears to be the receptor for an as yet unidentified growth factor.

Isolation of clones of normal and transforming alleles of the rat neu gene

Biologically active genomic clones of normal and transforming alleles of the rat neu gene have recently been isolated. Hung, M.-C, et al., *Proceedings of the National Academy of Sciences, U.S.A.,* 83:261-264 (1986). Structural comparison of these clones revealed no evidence of gross rearrangements, suggesting that subtle genetic alterations were responsible for activation of the neu oncogene. Comparable levels of p185 were shown to be expressed in nontransformed cell lines containing the normal allele and in transformed cell lines containing the mutant allele, suggesting that the alteration responsible for the activation of neu did not lead to deregulation of expression of the gene. Such results implicate a transforming lesion within the encoded protein p185, which should be represented in cDNA versions of the gene.

Comparison of cDNA clones of the normal neu gene and transforming cDNA clones

To determine the effect of the alteration responsible for activation of the neu gene, a comparison was made of the previously isolated transforming cDNA clone, DNAs from three other ethylnitrosourea-induced activations of the neu gene and a cDNA clone of the normal allele of neu.

Isolation of a normal neu cDNA clone

It was first necessary to isolate a normal neu cDNA clone. To do so, a cDNA library was constructed using RNA from the cell line DHFR G8. Hung, M.-C., et al., *Proceedings of the National Academy of Sciences, U.S.A.,* 83:261-264 (1986). The DHFR cell line was made by transfecting a genomic cosmid clone containing a complete normal neu gene from the BDIX strain of rat into NIH 3T3 cells. These cells express high levels of the neu gene product, p185 and a high level of the neu RNA transcribed from the transfected gene. cDNA clones were made by the S1 snapback technique, tailed with dCTP using terminal transferase, and inserted into dG-tailed pBR322 at the PstI site. Thirty recombinant plasmids reactive with neu probes were isolated.

These plasmid clones were compared by restriction mapping to a full length cDNA clone of an activated neu oncogene. While these normal cDNA clones have common sequences with the previously identified transforming cDNA clones, none contained the entire coding region of neu. A clone containing the entirety of the neu coding region was constructed, however, by in vitro recombination of two partial, overlapping clones which share a unique NaeI site. The 5' end of the resulting clone was sequenced to verify the presence of the initiation codon for the neu-encoded p185 protein.

This normal neu clone was inserted into the pSV2 expression vector to create pSV2neuN, as shown in FIG. 1. Mulligan, R. C. et al., *Nature,* 277: 108-114 (1979). A transforming neu cDNA clone derived from the B104-1-1 cell line, which is a secondary transfectant of an activated rat neu gene, was inserted into pSV2 to create a plasmid designated as pSV2neuT (FIG. 1). pSV2neuT was highly active in a focus-forming assay on NIH 3T3 cells or Rat 1 fibroblasts. This assay measures the ability of DNA molecules that have been introduced into cells by the transfection to convert such cells, growing in monolayer culture to a transformed state, causing descendants of these cells to form a cluster or focus of morphologically transformed cells in an area of the cell monolayer. However, when the normal neu cDNA, also inserted into the pSV2 vector, was transfected into NIH 3T3 cells using identical conditions, no foci were observed.

Comparison of p185 production by transformed and nontransformed cells

Figure 2B:
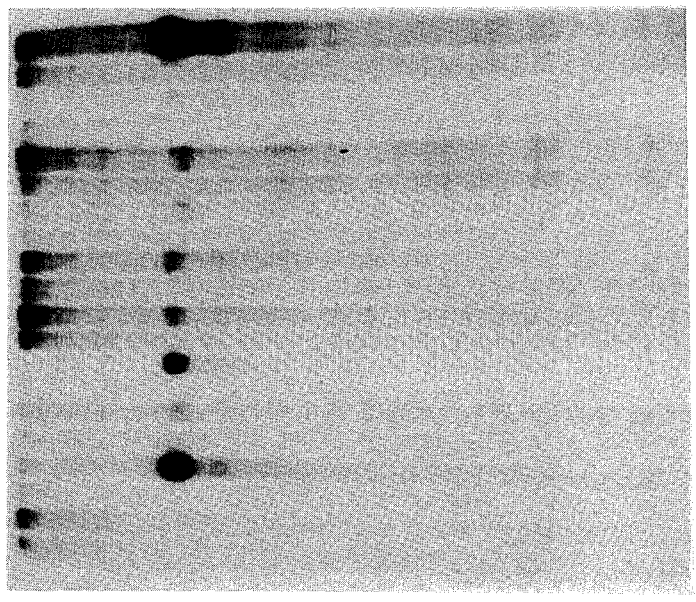
FIG. 2 presents electrophoretic gel patterns characteristic of cell lines containing pSV2neu constructions.

Cell lines containing the pSV2neuN or pSV2neuT plasmids were isolated by cotransfection with pSV2neo (referred to hereafter as the neo-r marker) and selection of G418. Southern, P. J. and P. Berg, *Journal of Molecular and Applied Genetics,* 1:327-341 (1982). Cell lines expressing the pSV2neuT construct were morphologically transformed and refractile; those containing pSV2neuN were flat and nontransformed in morphology. These cell lines were metabolically labeled with $^{32}P$ orthophosphate and their lysates incubated with a monoclonal antibody that specifically precipitates the rat neu gene product. As shown in FIG. 2B, lanes c, d, and i, the levels of labeled p185 were comparable in the transformed and nontransformed cells. These results are consistent with earlier work suggesting that neu has been activated by a mutation in the coding region of the gene rather than one which deregulates expression. Hung, M.-C. et al., *Proceedings of the National Academy of Sciences, U.S.A.,* 83:261-264 (1986).

Identification of the DNA sequences responsible for neu gene activation

Identification of sequences responsible for the transforming activity of the pSV2neuT clone was carried out by using recombinants between this clone and the pSV2neuN clone carrying the normal allele. The recombinants were constructed by ligation of appropriate cloned DNA segments. FIG. 1 shows the structure of a series of clones which delineate the region of neu that carries the activating mutation. The struture of each recombinant clone shown was verified by restriction mapping. In each case, at least two independent plasmid isolates were tested for the ability to morphologically transform NIH 3T3 cells. All recombinant clones were cotransfected with the neo-r marker and the morphology of the resulting G418-resistant colonies was scored. Morphologically nontransformed colonies were tested to ensure that they were expressing structurally intact p185 protein from the acquired cDNA clones.

Clones pSV2neuF and pSV2neuB, which contain the first 719 and 1899 nucleotides, respectively, of the transforming clone fused to the remaining sequences of the normal clone (FIG. 1), were not transforming, although they did direct the synthesis of p185. Clone pSV2neuH, which contained transforming neu sequences from the 5' end of the gene up to nucleotide 2387 and normal neu sequences thereafter, gave foci upon transfection and yielded transformed colonies indistinguishable from those generated by the parental pSV2neuT clone. pSV2neuC was also transforming. It contained an XbaI fragment from nucleotide 2337 to nucleotide 3534 of the normal neu gene, which replaced the corresponding portion of the transforming cDNA. These results indicate that the normal cDNA and the transforming cDNA differ in a sequence between nucleotides 1899 and 2337 and that the presence of this sequence in the transforming clone is necessary for transformation.

In order to prove that this sequence is also sufficient for transformation, the reciprocal constructs pSV2neuTN and pSV2neuNT (FIG. 1) were constructed and tested by transfection into NIH 3T3 cells and Rat 1 fibroblasts. pSV2neuTN contained the entire transforming cDNA with the exception of nucleotides 1899 to 2387, defined by NdeI and BglI sites, which are derived from the normal neu clone. pSV2neuNT contained the entire normal neu cDNA sequence except for the corresponding 488 nucleotides, which were replaced by those from the transforming clone. In parallel experiments, pSV2neuNT gave comparable numbers of foci to pSV2neuT, the parental transforming clone; pSV2neuTN, pSV2neuN, and mock transfected controls yielded no foci. These experiments demonstrate that the essential genetic differences between the normal and transforming clones reside within this 488 nucleotide fragment.

Figure 2A:
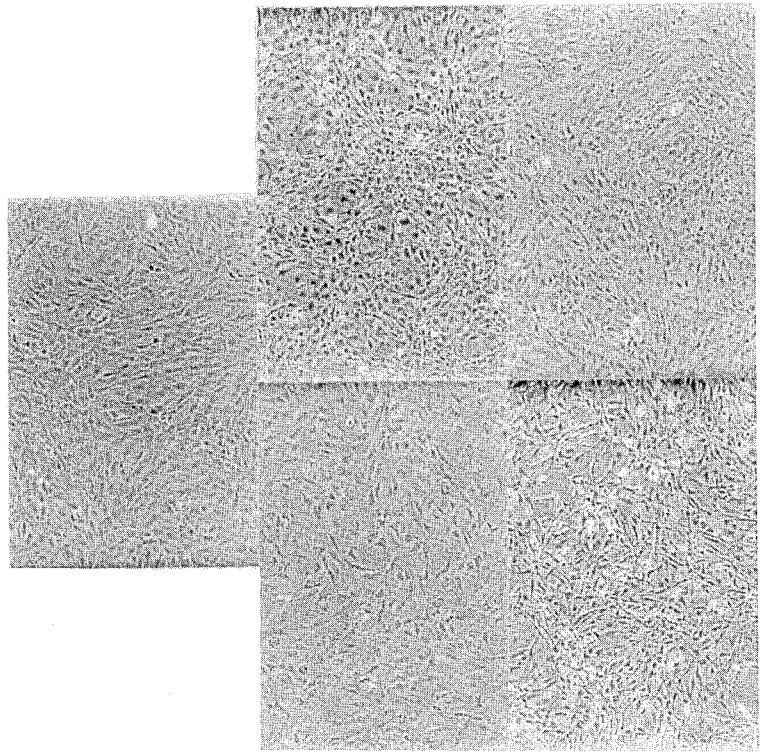

The data shown in FIG. 2 support these conclusions. G418-resistant cell lines isolated by cotransfection of the pSV2neu plasmids and the selectable neo-r gene are shown in FIG. 2A. Lines containing pSV2neuTN or pSV2neuN are morphologically flat and indistinguishable from lines transfected with the neo-r gene alone. In contrast, cells containing pSV2neuNT and pSV2neuT are highly refactile and very similar to one another in morphology. These cell lines were metabolically labeled with $^{32}$P-orthophosphate and the resulting lysates incubated with anti-p185 monoclonal antibody 16.4. Drebin, J. A. et al., Nature, 312:545-548 (1984). FIG. 2B shows the levels of p185 expressed in representative cell lines containing pSV2neuN (lanes c and d), pSV2neuT (lane i), pSV2neuTN (lanes e and f), and pSV2neuNT (lanes g and h). Lysates from DHFR G8 and B104-1-1 cells (lanes b and j), the cells lines from which the normal and transforming cDNAs were isolated, were also analyzed. Although individual cell clones show a wide range of p185 levels, it is clear that there are similar ranges of p185 expression in both the normal and transformed cells. No p185 is found in lines transfected with the neo-r marker clone alone (lane a). Thus, the differences in these cells must be accounted for by intrinsic differences in the properties of the p185 proteins that they express.

Definition of the mutation distinguishing the normal neu allele and the activated neu gene The complete DNA sequence of the coding region of the transforming neu cDNA has been determined. Bargmann, C. I. et al., Nature, 319:226-230 (1986). To define the precise mutation that distinguishes the two alleles, the DNA sequence of the region between nucleotides 1899 and 2387 was determined for the normal neu cDNA. Only a single difference was found between this sequence and that previously determined for the transforming clone. At nucleotide position 2012 there is an A in the oncogene clone, while the normal clone carries a T in this position. As a result, the predicted amino acid present at residue 664 of the encoded p185 is affected; a valine found in the normal protein is replaced by a glutamic acid in the oncogenic version. FIG. 3 shows the DNA and predicted amino acid sequence of nucleotides 1968 to 2073 for both the normal neu gene and the transforming neu gene. The presumed mutation falls within the putative transmembrane domain of the neu gene product, p185.

Genomic clones of normal and transforming alleles of neu have been previously isolated. These clones were used to independently verify the nucleotide difference seen in the cDNAs. Such corroborative data served to exclude the possibility that the observed difference in the cDNAs arose during cDNA cloning. Sequencing of subclones of the genomic versions of the two alleles confirmed that the same T to A substitution was present in these genomic clones. This indicates that the mutation, a T to A transversion, arose somatically during creation of the B104 neuroblastoma tumor or cell line.

Determination of activation of independent neu oncogenes

Earlier results had shown that DNAs prepared from four out of six neuro/gliobastoma cell lines displayed activated neu oncogenes in a NIH 3T3 focus assay. Shih, C. et al.: Nature, 290:261-264 (1981). These six cell lines had been derived by transplacental mutagenesis of BDIX rat embryos with ethylnitrosourea. These independent activated neu genes were evaluated to see if they contain the same activating mutation. DNAs from transfectants containing these neu genes were hybridized with oligonucleotide probes which would recognize preferentially one or the other allele of the neu gene. This technique has been successful in identifying various activated alleles of ras genes. Bos, J. L. et al., Nature, 315:726-730 (1985); Zarbl, J. et al., Nature, 315:382-385 (1985).

Oligonucleotides corresponding in sequence either to the wild type or the mutant neu version of the neu gene were synthesized. The sequence of these two 20-mers is given in FIG. 4. These 20-mers were then hybridized under stringent conditions (2 degrees below the calculated $T_m$ of a perfect duplex) to dried agarose gels containing DNAs which had been digested with appropriate restriction endonucleases. The 20-mer corresponding to the wild type sequences hybridized approximately ten times as well to pSV2neuN as it did to pSV2neuT. In contrast, the oligonucleotide whose sequence derived from the transforming allele preferentially hybridized to pSV2neuT by the same factor.

DNA was isolated from transfectants carrying the four independently activated neu oncogenes described above and cleaved with HindIII. The resulting fragments were resolved on a 1% agarose gel. The agarose gels were incubated under conditions identical to those used in analysis of the cloned DNAs described above shown in FIG. 4. DNA from DHFR G8, which contains about 50 copies per genome of the normal genomic neu gene, was included as a control.

Figure 5:
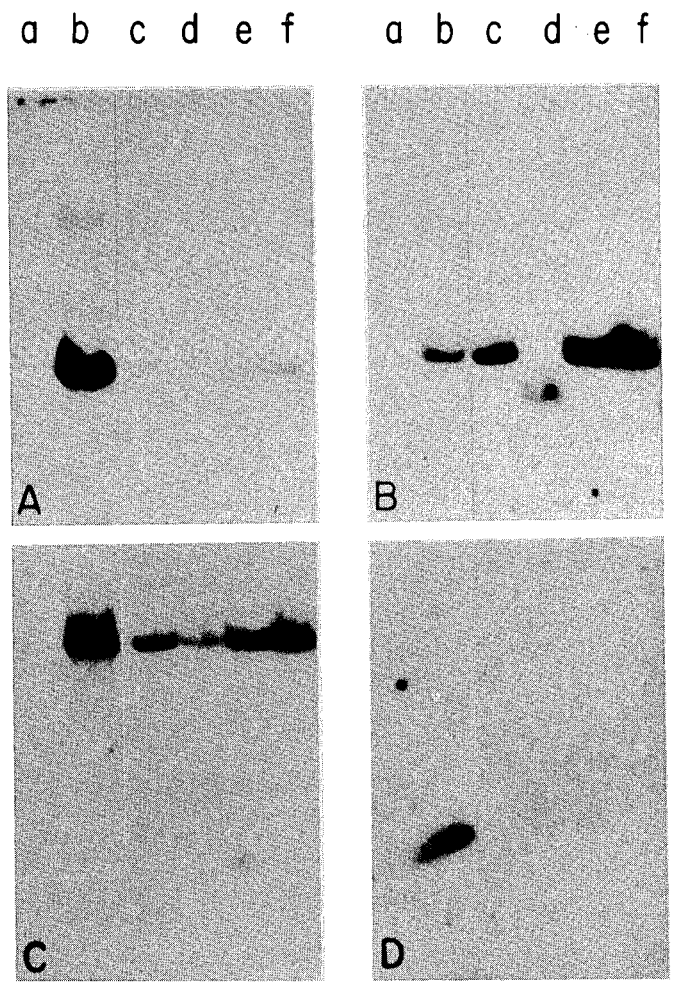
FIG. 5 shows electrophoretic gel patterns after hybridization of DNA from neu transfectants with oligonucleotide probes.

FIG. 5A shows hybridization of the transfectant DNAs with the oligonucleotide corresponding to the wild type sequence. A strong signal appears in DHFR G8 DNA, which has introduced copies of the normal neu gene (lane b). Considerably weaker signals can be seen in lanes containing the neutransformed transfectant DNAs (lanes c-f) and in untransfected NIH 3T3 cells (lane a). FIG. 5B shows an identical gel prepared in parallel probed with the oligonucleotide containing the mutant sequence. DHFR G8 DNA reacts only weakly with this probe (lane b) but all neu-transformed transfectant DNAs (lanes c to f) yield strong signals with this probe. The transfectant DNA shown in lane d has a smaller neu-homologous HindIII fragment than the other transfectants due to truncation of the transfected gene at the 3' end.

A low level of reactivity between the wild type probe and the transfectants is probably due to cross-reactivity of the probe, since it is comparable to the signal seen upon analysis of cloned pSV2neuT DNA with the same probe (compare FIG. 4 lanes b and d with lanes c-f in FIG. 5A and 5B).

In order to control for differences in signal intensity due to DNA loading and transfectant copy number, the gel in 5B was stripped of probe and rehybridized with an oligonucleotide probe from a different part of the neu gene. The transfectant cell lines may contain different copy numbers of the rat neu gene due to variable amplification during the process of transfection. The results of this hybridization are shown in FIG. 5C. Comparison of corresponding lanes in FIGS. 5A, B, and C shows that DNAs of all neu oncogene transfectants exhibit stronger hybridization with the mutant probe than with the wild type probe, and that the extend of their hybridization with the mutant probe correlates well with the copy number of the neu gene present in the various DNAs. Although these data strongly suggest that all of the activated neu genes studied have alterations at the same nucleotide position, it was not clear whether the mutations involved the same T to A transversion in all cases. A T to G transversion might give the same pattern of hybridization, since it would cause an A/G mismatch with the wild type oligonucleotide and a relatively stable G/T mismatch with the mutant oligonucleotide. To address this possibility, a third 20-mer was synthesized with the sequence shown in FIG. 4. This oligonucleotide was incubated under hybridizing conditions with the gel analyzed in FIG. 5A after the initial probe had been removed. This oligonucleotide did not hybridize preferentially to the transfectant DNAs under stringent conditions (FIG. 5D). Thus, the alteration in each of these activated neu genes is probably the same T to A transversion.

Figure 6:
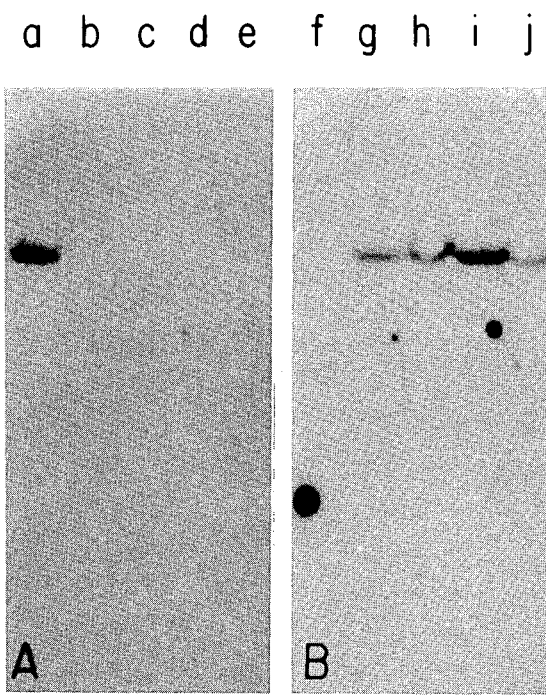
FIG. 6 shows electrophoretic gel patterns after hybridization of DNA from tumor cell lines and normal BDIX DNA with oligonucleotide probes.

That the point mutation was generated during tumorigenesis and thus did not reflect preexisting polymorphism in the rat genome or activation during the transfection process was also confirmed. DNA was isolated from BDIX rat liver and from the four rat tumor cell lines which were derived from BDIX rats and yielded activated neu genes in transfection assay. Duplicate gels were probed either with the wild type or the mutant oligonucleotide (FIG. 6). BDIX liver DNA reacts well with the wild type but not with the mutant oligonucleotide (FIG. 6, lanes a and f). In contrast, the four tumor cell lines react only with the mutant oligonucleotide (FIG. 6, lanes b-e and i-l). This demonstrates that the T to A transversion at nucleotide 2012 arose in the generation of the tumor or tumor cell lines. It also seems that the tumor cell lines are hemizygous or homozygous for the activated allele of the neu gene. Loss of the normal allele may have occurred during tumorigenesis or in passage of the tumor cell lines. A similar loss or underexpression of the normal ras alleles has been observed in several tumors and tumor cell lines that contain oncogenic versions of these ras genes. Capon, et al. *Nature,* 304:507–513 (1983): Guerrero, I et al., *Proceedings of the National Academy of Sciences, U.S.A.,* 82:7810–7814 (1985).

Multiple independent activations of neu

Chemical carcinogenesis, though provoked by apparently randomly acting agents, often results in specific genetic changes in the resulting tumor cells. Neu appears to be activated by the same nucleotide change in each of the four of the transforming neu alleles analyzed. Each of these alleles was isolated from a neuro- or glioblastoma that arose from transplacental exposure to the alkylating agent ethylnitrosourea. Schubert, D. et al., *Nature,* 249:224–227 (1974). Neu is also activated at the same residue in four independent nervous system tumors induced by the related alkylating agent methylnitrosourea.

Similarly, extensive study of methylnitrosoureainduced mammary carcinogenesis in Buf/N rats has shown that among nearly 100 independent resulting tumors, all contain H-ras oncogenes activated by the identical G to A transition at residue 35. Sukumar, S. et al., *Nature,* 306:658–661 (1983); Zarbl, H. et al., *Nature,* 315:382–385 (1985). Other examples of specificity of activation include dimethylbenzanthracene-induced papillomas with activated H-ras genes in genetically susceptible Sencar mice and thymic lymphomas induced by gamma irradiation or methylnitrosourea, which yield transfectable K-ras and N-ras oncogenes, respectively. Balmain, A. and I. A. Pragnell, Nature, 303:72–74 (1983); Guerrero, I. et al., *Proceedings of the National Academy of Sciences, U.S.A.,* 81:202–205 (1984). The K-ras oncogenes detected in the former case appear to have the same activating mutation in at least three out of four tumors examined. It is interesting to note that the administration of the same mutagen, methylnitrosourea, under different conditions leads to the specific activation of H-ras in mammary tumors, N-ras in thymic lymphomas, and neu in neurectodermal tumors. Guerrero, I. et al., *Science,* 225:1159–1162 (1984).

The carcinogen which induces each of these tumors must initially inflict widespread damage to the cellular DNA. The final mutation detected is, however, highly specific. Clearly, strong biological forces must act during multistep carcinogenesis to select the outgrowth of cells bearing the genetic lesions observed in the ensuing tumors. It appears that only a small proportion of cellular genes can be converted into biologically active oncogenes. Within one of these genes, only a few of many possible mutations will yield an actively transforming oncogene. The relatively rare mutations which do generate oncogenes are enriched first because they must confer a selective advantage to the tumor, and later because they can be detected in the focusforming assay.

The repeated appearance of a specific lesion in one tumor type suggests the presence of additional forces selecting among the possible activating mutations. The nature of the activating mutation must be strongly influenced by the chemical reactivities of the carcinogen. For example, different mutagens used to induce thymomas lead to different activated genes in the resulting tumors. Similarly, mammary carcinomas induced by dimethylbenzanthracene contain a different specific alteration from those induced by methylnitrosourea.

The reactivity of ethylnitrosourea, the agent which induced the described neuroblastomas, allows it to form a number of different adducts in DNA. Singer, B. and J. T. Kusmierek, *Annual Review of Biochemistry*, 52:655–693 (1982). Among these, an adduct causing G to A transition mutations is well described. Rajewsky, M. F., *Recent Results in Cancer Research*, 84:63–76 (1983). Such mutations have been found repeatedly as the activating lesions in the H-ras oncogenes of mammary carcinomas induced by the related carcinogen methylnitrosourea. Zarbl, H. et al., *Nature*, 315:382–385 (1985). The presently described mutations are, however, T to A transversions, the creation of which must be explained by alternative mechanisms involving another one of the many adducts formed after administration of these alkylating agents. This type of mutation is not without precedent: two other ethylnitrosoureainduced mutations isolated after germ-line mutagenesis of mice have also been shown to be T to A transversions. Popp, R. A. et al., *Genetics*, 105: 157–167 (1983); Lewis, S. E. et al., *Proceedings of the National Academy of Sciences, U.S.A.*, 82:5829–5831 (1985). An N-ras oncogene isolated from a methylnitrosourea-induced lymphoma has been found to be activated by a C to A transversion suggesting that several different adducts induced by alkylating agents can lead to mutations. Guerrero, I. et al., *Proceedings of the National Academy of Sciences, U.S.A.*, 82:7810–7814 (1985).

Although the discussion to this point, as well as the experimental work described, has been related to the point mutation responsible for activation of the rat neu oncogene, it is possible to use the same approach in identifying the corresponding activation mutation in human neu genes and in detecting the presence of a neu oncogene (or its corresponding protooncogene) in human tumor cell DNAs. For example, oligonucleotide probes can be constructed which are specifically reactive with the region of a human neu gene which corresponds to the region shown to contain the point mutation responsible for the activation of the rat neu oncogene. An example of a probe which can be constructed is one based on a single nucleotide difference between a neu oncogene and its protooncogene, this single nucleotide alteration being responsible for conversion of the neu protooncogene into its activated oncogene form. These probes, which can be of any length but will generally be 15 to 20 nucleotides long, can then be used to analyze a tumor cell genome, to determine whether it carries lesions (mutations) in the neu oncogene and to determine their precise location, as described above for the rat neu oncogenes. An assay for detecting carcinogenesis caused by mutation of a neu protooncogene into neu oncogene comprises employing a labelled oligonucleotide probe specific for a nucleotide sequence present in (or transcribed from) the protooncogene or the oncogene, but not the other. An assay for carcinogenesis in human cells can be performed by isolating DNA from the test cells and contacting the DNA with a labelled polynucleotide probe specific for either an oncogenic or protooncogenic sequence in the DNA and thereafter determining whether the probe hybridizes to the DNA. After being radiolabelled, these probes can be used, for example, in the Southern blot procedure to assess tumor cell DNAs for the occurrence of such point mutations. This type of assay can be used in a clinical context as a diagnostic tool to determine the profile of oncogenes activated in human tumor DNAs. The assay would be highly specific because it is capable of detecting single nucleotide alterations in genes of the neu family, thus providing very definitive information about the tumor cells being assayed.

Reagents for employing these oligonucleotide probes can be assembled into a kit. Thus, a kit might contain, in addition to the probe, one or more buffers, reagents for labelling the probe, reagents employed in Southern or other blots, etc.

Because of the change in amino acid sequence of the product protein encoded by a protooncogene from the product encoded by an oncogene, it is possible to detect either by specific serological reagents. The serological reagents can be specific for the normal, neu protooncogene-specified amino acid sequence at this site of the protein, or be specific for the altered oncogene-specified amino acid sequence at this site of the protein. Other serological reagents could be employed that are reacted with a region of the protein that is unaltered, and consequently reactive with either normal or abnormal forms of the encoded protein.

Using cloning techniques, significant amounts of the protein encoded for by the normal site of the protooncogene, or by the altered site of the oncogene, can be isolated. Such protein segments could be used to produce antibodies by standard antibody production techniques. Thus, for producing polyclonal antibodies, such proteins would be employed to immunize a host, such as a rabbit or a rat, and antibodies to the protein would be collected from serum obtained from the host.

Alternatively, monoclonal antibodies could be produced employing cells which produce antibodies to the protein produced by the isolated gene segment in typical fusion techniques for forming hybridoma cells. Basically, these techniques involve the fusing of the antibody-producing cell with a cell having immortality, such as a myeloma cell, to provide a fused cell hybrid which has immortality and is capable of producing the desired antibody (in this case, an antibody to the normal or altered segment of protein coded for by the isolated gene segment). The hybrid cells are then cultured under conditions conducive to the production of antibody after which antibody is collected from the cell culture medium. Such techniques for producing monoclonal antibodies have been well described in the literature. See, for example, U.S. Pat. Nos. 4,172,124 and 4,196,265, issued to Hilary Koprowski et al., the teachings of which are hereby incorporated by reference.

We claim:

1. An oligonucleotide probe capable of hybridizing specifically with the region of mutational activation in a neu gene of mammalian origin, the region of mutational activation being within that portion of the gene encoding the transmembrane domain of the gene product.

2. An oligonucleotide probe of claim 1 which is labelled.

3. An oligonucleotide probe of claim 2 which is radiolabelled.

4. An oligonucleotide probe which is capable of hybridizing specifically with a nucleotide sequence present in a region of a neu oncogene of mammalian origin but not present in the corresponding region of the protooncogene for that neu oncogene, said region of the oncogene and the protooncogene being that region encoding the transmembrane domain of the gene product.

5. An oligonucleotide probe of claim 4 which is labelled.

6. An oligonucleotide probe of claim 5 which is radiolabelled..

7. An oligonucleotide probe comprising from 15 to 20 nucleotides, the probe being capable of hybridizing specifically with a region of a neu oncogene of mammalian origin which differs from the corresponding of the protooncogene of said oncogene by a single nucleotide substitution, said substitution causing activation of the neu oncogene, and said region being within that portion of the gene encoding the transmembrane domain of the gene product.

* * * * *

UNITED STATES PATENT AND TRADEMARK OFFICE
CERTIFICATE OF CORRECTION

PATENT NO. : 4,935,341

DATED : June 19, 1990

INVENTOR(S) : Bargmann, et al

It is certified that error appears in the above-identified patent and that said Letters Patent is hereby corrected as shown below:

Col. 14, claim 7, line 6, after "corresponding" insert --region--.

Signed and Sealed this

Twenty-fourth Day of September, 1991

Attest:

HARRY F. MANBECK, JR.

Attesting Officer

Commissioner of Patents and Trademarks